United States Patent
Kittel et al.

(10) Patent No.: US 11,105,729 B2
(45) Date of Patent: Aug. 31, 2021

(54) SENSOR FOR MEASURING THE EMBRITTLEMENT OF STEELS BY HYDROGEN IN AN AGGRESSIVE ENVIRONMENT, SAID SENSOR COMPRISING A METAL CAVITY CONNECTED TO A PRESSURE-MEASURING DEVICE

(71) Applicant: IFP Energies nouvelles, Rueil-Malmaison (FR)

(72) Inventors: Jean Kittel, Lyons (FR); Gilbert Parrain, Diemoz (FR); Christian Boudou, Mions (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 588 days.

(21) Appl. No.: 15/774,459

(22) PCT Filed: Oct. 20, 2016

(86) PCT No.: PCT/EP2016/075200
§ 371 (c)(1),
(2) Date: May 8, 2018

(87) PCT Pub. No.: WO2017/080780
PCT Pub. Date: May 18, 2017

(65) Prior Publication Data
US 2020/0256786 A1    Aug. 13, 2020

(30) Foreign Application Priority Data
Nov. 9, 2015 (FR) .................................... 1560718

(51) Int. Cl.
*G01N 17/00* (2006.01)
*G01N 33/2025* (2019.01)

(52) U.S. Cl.
CPC ....... *G01N 17/006* (2013.01); *G01N 33/2025* (2019.01)

(58) Field of Classification Search
CPC ............... G01N 33/203; G01N 17/006; G01N 33/2025; G01N 33/20; G01N 2500/04;
(Continued)

(56) References Cited

U.S. PATENT DOCUMENTS 4,416,996 A    11/1983  Von Klock et al.
5,279,169 A     1/1994  Freeman
(Continued)

FOREIGN PATENT DOCUMENTS

JP        2790702 B2      8/1998
JP    2011179893 A       9/2011
(Continued)

OTHER PUBLICATIONS

International Search Report for PCT/EP2016/075200, dated Nov. 29, 2016; English translation submitted herewith (7 pgs.).

*Primary Examiner* — Melissa J Koval
*Assistant Examiner* — Trung Q Nguyen
(74) *Attorney, Agent, or Firm* — Fitch, Even, Tabin & Flannery LLP

(57) ABSTRACT

The present invention is a sensor for measuring a risk of hydrogen embrittlement of industrial equipment including a metallic wall in a reactor or in a pipeline comprising a body having a closed cavity including an end containing a pressure sensor which measures pressure within the closed cavity, the metallic wall having a wall thickness measured between inner and outer surfaces thereof, and wherein a ratio of thickness of the metallic wall to thickness of the industrial equipment ranges from 1/3 to 1/10.

16 Claims, 6 Drawing Sheets a) Cracking test
Measurement of the crack area under different conditions (different test solutions).

b) Pressure measurement test
Measurement of the equilibrium pressure under different conditions (different test solutions).

(58) Field of Classification Search
CPC .. G01N 33/582; G01L 19/0023; G01D 11/30; G01F 15/14; G01F 15/18; H01L 21/0445
USPC .. 324/500, 600, 700, 750.3, 765.01, 761.01, 324/76.11, 76.37, 425–450; 73/86, 73/152.57, 723, 590, 580, 865.8, 623, 73/61.41; 436/2–8, 43, 84, 125, 163, 436/164, 166, 172, 501
See application file for complete search history.

(56) References Cited

U.S. PATENT DOCUMENTS

| | | | |
|---|---|---|---|
| 6,058,765 | A | 5/2000 | Yepez et al. |
| 6,537,824 | B1 | 3/2003 | Correa |
| 2008/0233010 | A1 | 9/2008 | Blencoe et al. |
| 2009/0302857 | A1* | 12/2009 | Harada ............. G01N 27/4074 324/444 |
| 2013/0189763 | A1* | 7/2013 | Dalla-Betta ............ C12M 29/02 435/252.1 |
| 2013/0236975 | A1 | 9/2013 | Roumeau et al. |
| 2018/0313779 | A1* | 11/2018 | Mohamed Shibly ........................ G01N 27/4072 |

FOREIGN PATENT DOCUMENTS

| | | |
|---|---|---|
| JP | 2013044712 A | 3/2013 |
| JP | 2013044716 A | 3/2013 |
| JP | 2015090314 A | 5/2015 |
| WO | 2013012364 A1 | 1/2013 |

\* cited by examiner a) Cracking test
Measurement of the crack area under different conditions (different test solutions).

b) Pressure measurement test
Measurement of the equilibrium pressure under different conditions (different test solutions).

SENSOR FOR MEASURING THE EMBRITTLEMENT OF STEELS BY HYDROGEN IN AN AGGRESSIVE ENVIRONMENT, SAID SENSOR COMPRISING A METAL CAVITY CONNECTED TO A PRESSURE-MEASURING DEVICE

CROSS REFERENCE TO RELATED APPLICATION

Reference is made to PCT/EP2016/075200 filed Oct. 20, 2016, and French Application No. 15/60.718 filed Nov. 9, 2015, which are incorporated herein by reference in their entirety.

BACKGROUND OF THE INVENTION

Field of the Invention

The present invention relates to a sensor for measuring risk of hydrogen embrittlement (HE) of a metal in an aggressive environment promoting the penetration of hydrogen into the metal. The sensor is exposed to an aggressive environment capable of causing hydrogen embrittlement for metal of a metal body.

Description of the Prior Art

Hydrogen penetration into the metal from the external medium leads to the diffusion of hydrogen into the metal of the sensor, then recombination thereof as gaseous hydrogen inside the closed cavity.

The measurement of the steady-state pressure reached within this cavity is thus indicative of the hydrogen activity in the steel.

In order to assess the risks of hydrogen embrittlement on items of industrial equipment, two broad categories of methods are mainly used:
  periodic inspection using non-destructive testing tools; and
  the use of sensors intended to assess hydrogen flows passing through the metal.

The main purpose of periodic inspection is to detect the presence of any cracks, with a detection threshold that is as small as possible, and/or to monitor the change over time of cracks already detected during a previous inspection.

This type of method however has quite a high level of risk, linked on the one hand to the generally rapid nature of the propagation of cracks after initiation, and on the other hand to the localized nature of the cracks, with the consequent high probability of not detecting the cracks with an inspection that rarely covers the items of equipment in their entirety.

As a result, specific inspection for HE is often restricted to the items of equipment for which the consequences of cracking are not too serious; for example items of equipment under moderate pressure, with less hazardous fluids.

The use of specific sensors allows more regular monitoring. With regard to hydrogen embrittlement, the parameter most often used is the hydrogen flow passing through a metal membrane.

In fact, as indicated in the introduction, hydrogen embrittlement of metals originates from the penetration of hydrogen from the aggressive medium into the inside of the steel. This inflow proves relatively easy to measure with devices using permeation through a membrane, by direct application of Fick's diffusion laws.

The sensors used generally are a steel membrane in which one of the faces is exposed to the hydrogenating medium while the other face is maintained under conditions allowing hydrogen to flow out again, with a device for measuring this output flow. In the theoretical case of diffusion of hydrogen without interaction with the metal (purely interstitial diffusion), measuring the steady-state flow (Js) makes it possible to estimate the hydrogen concentration in the metal at the level of the input face (CO) from the relationship:

$$J_s = D \frac{C_0}{l} \quad \text{(Equation 1)}$$

In equation (1) D is the hydrogen diffusion coefficient in the metal in question, and $l$ is the thickness of membrane to be passed through.

Several types of devices for measuring the output hydrogen flow from the membrane are used.

The most frequently listed in the scientific literature are electrochemical devices, for which the hydrogen output metal face is placed in contact with an electrolytic solution and is maintained at a potential at which oxidation of the hydrogen atoms occurs spontaneously and generates an electrical current that can be measured by a device of the ammeter type.

The principles of this electrochemical measurement were introduced in a 1964 publication by Devananthan and Stachurski [1]. This type of device is not very suitable for applications for monitoring items of equipment in service, due to its complex implementation, which requires the use of a measurement chamber filled with an electrolyte solution and equipped with a system for electrochemical measurements.

Several patents however propose methods for monitoring hydrogen embrittlement utilizing these electrochemical measurement principles, such as for example Japanese patents 2011/179893A, 2013/044712A, and 2013/044716A.

Devices utilizing pressure measurement. In this case, the hydrogen output face opens into a sealed enclosure in which the pressure is measured, and the hydrogen flow can then be deduced from the rate of pressure increase. This type of sensor is generally equipped with a purge system in order to regularly remove the hydrogen accumulated in the sensor and which maintains a maximum hydrogen gradient within the membrane.

This principle is applied for example in U.S. Pat. No. 5,279,169 or in U.S. Pat. No. 6,537,824.

Devices implementing a measurement of the volume of hydrogen in a closed cavity partially filled with a liquid are disclosed in U.S. Pat. No. 4,416,996.

The change in volume thus gives a direct measurement of the output hydrogen flow from the membrane, and this flow can then be used in order to estimate the risks of hydrogen embrittlement.

Application of a measurement of hydrogen flow in order to assess the risks of hydrogen embrittlement of mechanical parts subject to cyclical mechanical stresses is also mentioned in patent WO13012364A1, although the method for measuring hydrogen flow is not specified.

Assessment of the corrosion rate of the inner metal wall is another application frequently mentioned for the aforementioned devices which measure a hydrogen flow through a metal wall. The principle of these measurements is based on the link between the quantity of hydrogen that enters the steel and the corrosion rate.

This link is relatively direct, for example in the case of corrosion in an acid aqueous medium, where the cathodic reaction is the reduction of the proton giving an atom of hydrogen which can then enter the metal and diffuse. Such methods for monitoring corrosion are thus mentioned in U.S. Pat. No. 6,058,765, and US published application 2013/236975A.

Certain limits can be identified for the aforementioned devices of the prior art.

First, the measured variable is still hydrogen flow through a metal wall. A correlation is then proposed between the value of this flow and the risk of hydrogen embrittlement or the corrosion rate of the inner wall. Now, this link is by no means direct.

It is in fact known to persons skilled in the art that hydrogen embrittlement leading to cracking (phenomenon of "blistering" or "hydrogen-induced cracking" denoted HIC) is largely linked to the quantity of absorbed hydrogen in the metal, and to its chemical activity in the metal.

The initiation of cracking requires a sufficient concentration of absorbed hydrogen in the metal to be reached. Although the value of the hydrogen flow is one of the most easily measurable parameters, nonetheless this does not mean it is the most relevant. In fact, this indicates the rate with which hydrogen enters the metal, but in no way indicates the limit value (concentration or activity of absorbed hydrogen) that will be reached in the steady state. This hydrogen activity or concentration value in the steady state is denoted Ce. It corresponds to an internal hydrogen pressure (by application of Sieverts' law), which is denoted in the remainder of the text equilibrium pressure, or Pe. Now, in fact, it is the increase in internal hydrogen concentration above a given threshold (denoted threshold concentration Cs or threshold pressure Ps, according to whether the concentration or activity values, or the pressure values are used, the relationship of which is defined by Sieverts' law,) that influences the cracking or the absence of cracking.

This equilibrium concentration (Ce) value can be estimated using flow measurements, but in a fairly approximate manner, making numerous simplifying hypotheses with respect to the method of diffusion, the diffusion coefficient and the wall thickness, assuming that the equilibrium concentration (Ce) is equal to the concentration of absorbed hydrogen in the metal at the level of the input face (C0) calculated based on flow measurements and by using Equation (1).

Steel will be referred to herein most frequently, without being a limitation to this particular metal.

Hydrogen embrittlement is a relatively frequent phenomenon causing damage of items of industrial equipment made from metal materials, sometimes with disastrous consequences. The physical origin of this phenomenon arises from the ease with which hydrogen diffuses into most metals, as a result of its very small size (it is the smallest atom). When the aggressive environments to which the metals are subject contain hydrogen, the latter is then eventually able to penetrate the steel.

This affects a wide variety of environments, for example: a gaseous medium containing hydrogen, corrosive aqueous media in which a reduction reaction involving a hydrogen-containing compound (such as water or such as H+ ions in an acid medium) occurs.

Once in the steel, hydrogen can then diffuse quite easily, and may accumulate in metallurgically favorable areas, such as crystalline defects (dislocations, disconformities, deposits), grain boundaries, inclusions.

This hydrogen accumulation leads to weakening of the mechanical properties of the metal.

If the metal is subject to (external or residual) stresses, and the hydrogen-associated mechanical strength drops below that required for the stresses applied, local cracking can occur. The stresses in question can have different sources: local residual stresses associated with the metallographic defects, stresses originating from shaping steps, service stresses of the items of equipment (weight, internal pressure, etc.). Then, when the accumulation of gaseous hydrogen under high pressure in the cavities forms, propagation of the cracking can occur.

This type of cracking represents a significant challenge in industry, inasmuch as this is generally a sudden phenomenon, without obvious signs beforehand, capable of leading to complete rupture of the item of equipment. There is thus a genuine interest in the availability of a sensor allowing forewarning of the onset of this rupture risk.

SUMMARY OF THE INVENTION

The present invention makes possible measurement of the risk of hydrogen embrittlement of metals used in different types of industrial installations such as pipelines for the transportation of crude or hydrocarbon-containing products, or chemical reactors such as hydrotreating reactors which can operate up to pressures of several hundred bars.

If the admissible limit for hydrogen content in the metal in question is known, the sensor according to the invention thus makes it possible to verify in real time that this level is not reached in service.

More specifically, the sensor according to the present invention can be defined as a sensor for measuring the risk of hydrogen embrittlement of a metal item of industrial equipment (simply called metal in the remainder of the text) comprising the following elements:
  a metal body, in which a closed cavity is produced, which communicates at one of its ends with a device for measuring pressure; and
  a device for measuring pressure connected to the cavity and allowing the pressure to be measured inside the cavity,
the cavity has a thickness comprising a ratio between 1/3 and 1/50, and preferably between 1/4 and 1/10 of the thickness of the item of industrial equipment to be assessed.

The sensor according to the invention can be applied in particular to measuring the risk of embrittlement of steels used in different items of industrial equipment. But it could also be used for measuring the risk of embrittlement of other metal materials.

Generally, the hollow metal body constituting the embrittlement sensor according to the invention must have geometrical features providing a large surface area of metal exposed to the external medium, a cavity with a limited volume in order to allow a rapid pressure increase for a given input hydrogen flow, and the smallest possible wall thickness in order to allow the greatest possible flow.

The wall thickness is defined as the thickness measured between the inner and outer surfaces of the cavity.

For a sensor according to FIG. 1, the ratio of the volume of the cavity to the surface exposed to the hydrogenating aggressive medium must preferably be comprised between 0.01 and 0.5 cm.

Preferably, the metal used for producing the sensor is the same as the metal of the item of industrial equipment to be assessed.

According to a variant of the present invention, the sensor for measuring the risk of hydrogen embrittlement of a metal can be produced directly in a part of the item of industrial equipment to be assessed, for example in a part of the reactor wall or in a part of the pipeline wall.

The present invention also relates to a method for assessing the risk of hydrogen embrittlement of a metal in a given environment, using the sensor according to the invention, in which the steps below are followed:

Step 1: for a given metal, cracking tests are carried out in hydrogenating environments presenting increasing risks of hydrogen embrittlement, in order to obtain on the one hand, the conditions for which cracking is absent, and on the other hand, the conditions for which cracking is present;

Step 2: in the same hydrogenating environments as for step 1, pressure measurement tests are carried out using a sensor according to the invention, produced from the same metal as that used for step 1, and the $H_2$ equilibrium pressure (Pe) is measured for each environment;

Step 3: for each environment, the results of the cracking tests and the pressure measurement tests are compared, and the minimum pressure corresponding to cracking situations is determined. This minimum pressure is considered to be the threshold value for crack resistance for steel under consideration, and is denoted Ps.

Step 4: the embrittlement sensor produced from the same metal is exposed to a given environment, and the change over time of the pressure in the sensor is monitored until it reaches a plateau where it remains constant. This equilibrium pressure is denoted Pe.

Step 5: then the equilibrium value Pe is compared with the threshold value Ps obtained in step 3:

If Pe is less than Ps, there is no risk of cracking of the steel under the conditions in question if Pe is greater than Ps, there is a risk of cracking.

The sensor according to the present invention can be used for assessing the risk of embrittlement of steels subject to gaseous environments containing 112 or $H_2S$, or to liquid environments containing dissolved $H_2S$ and having pH values from 3 to 8, and preferentially from 4 to 7.

Purely by way of illustration, the sensor according to the invention can be used in an aggressive environment of the same nature as that of the industrial installation to be monitored, for example an aqueous medium containing dissolved $H_2S$ such as found in oil production, Still by way of illustration and non-limitation, the sensor according to the invention can be used in an aggressive environment of the same nature as that of the industrial installation to be monitored, for example a high-temperature gaseous medium containing hydrogen such as found in refining processes.

DETAILED DESCRIPTION OF THE INVENTION

The present invention is a sensor and a method of use of this sensor, for assessing the risk of hydrogen embrittlement for a given metal in an aggressive environment promoting the penetration of hydrogen into the metal.

The sensor according to the invention is constituted by a metal body containing a closed cavity connected to a device for measuring pressure. This sensor is intended to be exposed to an aggressive environment capable of causing hydrogen embrittlement for the metal constituting the metal body.

The penetration of hydrogen from the external medium leads to the diffusion of hydrogen into the metal of the sensor, then recombination thereof as gaseous hydrogen inside the closed cavity.

The measurement of the steady-state pressure (Pe) reached within this cavity is thus indicative of the hydrogen activity in the steel. If the acceptable threshold for hydrogen content in the metal in question is known (Ps), the sensor then allows real-time verification that this level has not been reached in service.

Figure 1:
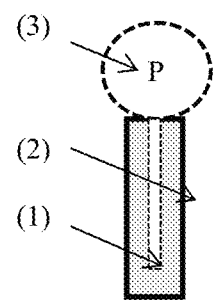
FIG. 1 shows a diagrammatic view of the sensor according to the invention, which has a tubular shape and is connected to a pressure sensor. The tubular shape is practical, but other shapes could be used such as for example spherical or planar.
Figure 1A:
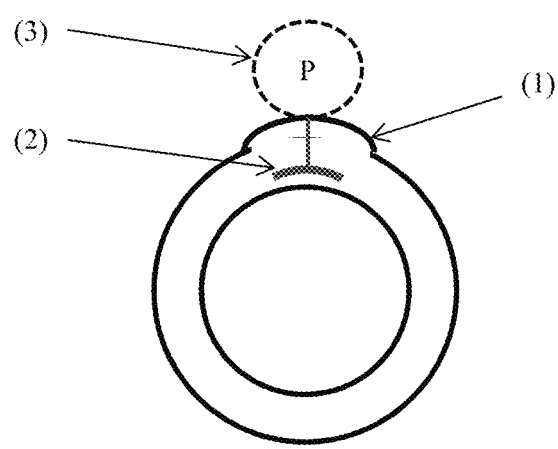
FIG. 1A shows a diagrammatic view of the sensor according to the invention when it is directly integrated with the item of industrial equipment to be characterized. In this case the sensor according to the invention is arranged in a portion of the item of equipment to be characterized with this portion being provided if necessary with an additional thickness.

The present invention therefore describes an embrittlement sensor the main constituents of which are shown diagrammatically in FIG. 1 or in FIG. 1A, according to the version used.

This sensor contains:
(1) a metal portion, chosen in the same grade of metal as the installation for which it is desired to assess the risk of hydrogen embrittlement. In normal use, this metal portion is exposed to the hydrogenating corrosive medium.
(2) a cavity having a small volume, arranged inside the metal portion (1).
(3) a device for measuring pressure inside the cavity.

The approach of the present invention is very different in nature than the data used and in the interpretation of the data than compared to the prior art.

In fact, while currently normal practice determines the flow of hydrogen, herein direct use of the measurement of the equilibrium pressure within the cavity is performed in order to assess the absorbed hydrogen activity in the steel.

In fact, by application of Sieverts' law, the activity of a gaseous element dissolved in a metal is directly proportional to the square root of the pressure of this same gas in equilibrium with the metal, therefore corresponding to the equilibrium pressure (Pe) generated by this gas within the measurement cavity. As a result, the equilibrium pressure measurement inside the cavity of the sensor can be directly correlated with the hydrogen activity or concentration in the steel at equilibrium (Ce). Now, the risk of internal cracking of the "blistering" or "hydrogen-induced cracking (HIC)" type is directly linked to the hydrogen activity in the steel. This pressure measurement therefore corresponds to a direct measurement of the severity of the risk of hydrogen embrittlement.

Another differentiating element of this invention is based on the use of the same metal for the body of the sensor as that of the item of industrial equipment to be monitored. In fact, for measurements of the hydrogen flow according to the prior art, the nature of the metal constituting the steel membrane can equally well be selected from a metal grade close to that of the metal of the item of equipment to be monitored, but not necessarily identical thereto. Now, the nature of the metal can affect the hydrogen diffusion and solubility properties, and in particular the acceptable threshold content before cracking occurs.

The values for threshold concentration (Cs) or threshold pressure (Ps) defining the absorbed hydrogen value above which the metal is likely to crack, are in fact specific to each metal or each grade of steel. The same applies for steady-state concentrations and pressure (Ce and Pe).

It is therefore important to use a representative metal for the device, preferably the same metal as will be used for the item of industrial equipment.

The use of the sensor according to the invention is thus based on prior knowledge of the hydrogen embrittlement resistance range of the metal in question, which can be determined by any hydrogen embrittlement test method well known to a person skilled in the art.

Among these methods there may be mentioned for example the test described in NACE TM0284 (NACE International) which describes carrying out tests for the HIC cracking behavior of low-alloy steels in an aqueous medium containing dissolved $H_2S$.

This pressure threshold value (Ps) can be characterized by using a sensor device according to the invention, as illustrated in Example 2. Once the threshold value for hydrogen activity or pressure (Cs or Ps) is known for a given metal, the sensor device according to the invention can be used in order to ensure that this limit value is not exceeded in service.

In order to pre-empt risks, it is important for the thicknesses of the walls of the sensor to be less than the thicknesses of metal of the installation to be monitored, and for the volume of the cavity to be as small as possible. Under such conditions, the time taken to reach the equilibrium pressure (Pe) in the sensor is faster than the time taken to reach the same pressure level in the actual installation, thus making it possible to pre-empt risks.

EXAMPLES ACCORDING TO THE INVENTION

Example 1 according to the prior art: low-allow steel with high elastic limit In this example, the body of the sensor was produced from low-alloy steel with a high elastic limit Its micro-structure is ferrito-pearlitic. This type of steel is very susceptible to internal hydrogen cracking when used in the presence of water containing dissolved $H_2S$.

These risks depend mainly on the pH of the solution and the $H_2S$ content.

Two tests for crack-resistance (HIC or "hydrogen-induced cracking") were conducted on this steel in an aqueous solution with 35 g/L NaCl at pH 4.5 under an $H_2S$ partial pressure of 10 mbar (test 1) and 50 mbar (test 2). These tests were conducted according to the NACE TM 0284 method well known to a person skilled in the art, and with immersion periods of 1 month. For test 2 (50 mbar of $H_2S$) they showed significant cracking of the steel, while for test 1 (10 mbar of $H_2S$), no cracking was noted.

Tests according to the prior art, utilizing a pressure sensor used in order to determine a hydrogen flow through the steel, were then conducted in an aqueous solution of the same composition as for the previous tests (35 g/L NaCl, at pH 4.5) and varying the $H_2S$ composition from 10 to 50 mbar during the test. These test conditions thus correspond to starting the test in an environment in which the material is not susceptible to internal cracking (pH 4.5 and 10 mbar of $H_2S$), then passing to an environment in which the material is susceptible to cracking (pH 4.5 and 50 mbar of $H_2S$).

Figure 2:
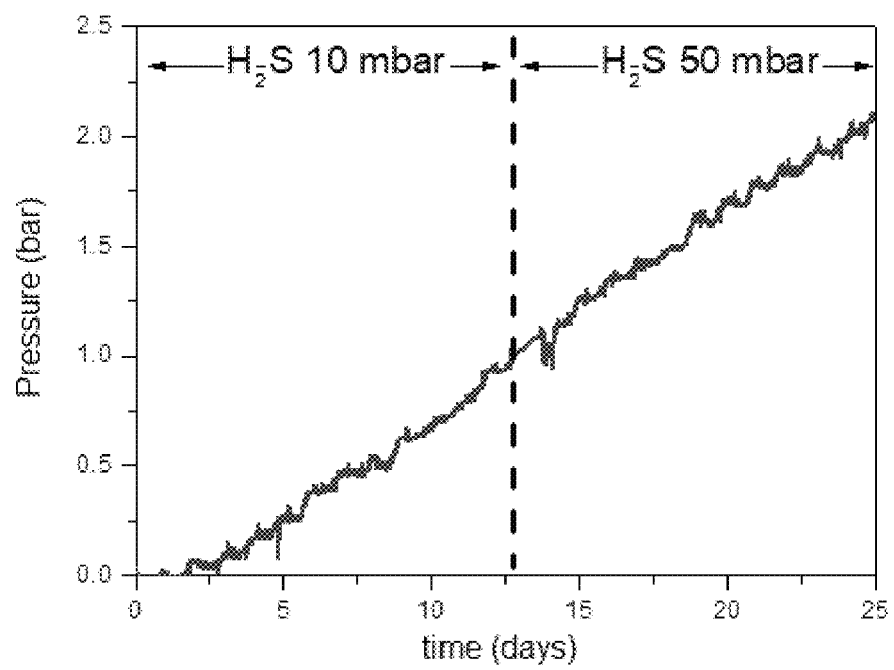
FIG. 2 shows an example of the change over time of the internal pressure in a hollow sensor made from low-alloy, high elastic limit steel according to the invention. This sensor is subject to a corrosive environment constituted by water at 35 g/L NaCl at pH 4.5 and containing 10 then 50 mbar dissolved $H_2S$. This type of environment is known to promote the entry of hydrogen into the steel. It originates in this case from the electrochemical proton reduction reaction (H++e−→H).

The curve of the change in internal pressure measured throughout this test is shown in FIG. 2.

This curve reveals that the change in $H_2S$ content from 10 to 50 mbar is not reflected in a change in the rate of pressure increase. This rate of pressure increase is a direct reflection of the hydrogen flow passing through the metal wall. This flow value is quoted in the prior art for characterizing the risk of hydrogen embrittlement. This example thus shows that the use of a simple flow measurement sensor as described in the state of the art does not make it possible to detect a difference between these two corrosive environments, since the first, under 10 mbar of $H_2S$, does not present a cracking risk for this steel, while conversely the second, under 50 mbar of $H_2S$, leads to significant cracking of this steel.

This illustrates the limits of the current practices described in the prior art, of using only flow measurements. The second example is intended to illustrate more directly the benefit of the equilibrium pressure measurements by using the sensor according to the invention.

Example 2 According to the Invention: Low-Alloy Steel for Pipeline Plate of API 5 L X65 Type In this example, the tested steel is a low-alloy steel of API 5 L X65 type, commonly used for the manufacture of oil and gas transportation pipelines. This steel presents risks of hydrogen embrittlement when it is used in the presence of water containing dissolved $H_2S$.

These risks depend mainly on the pH of the solution and the $H_2S$ content.

Tests for crack-resistance (HIC or "hydrogen-induced cracking") were conducted on this steel in solutions with a pH varying between 4.5 and 6.5, under a partial pressure of H$_2$S of 100 mbar.

These tests were conducted on steel coupons of 100 mm long, 20 mm wide, and thickness equivalent to the thickness of the plate (i.e. 17 mm) according to the NACE TM 0284 method well known to a person skilled in the art, and with immersion periods of 1 month.

These tests according to the prior art make it possible to verify, for a given corrosive environment, if the steel presents risks of internal cracking. In the case of cracking, this can be quantified for example by ultrasound non-destructive testing. The extent of the cracking is then expressed as a percentage of surface area cracked in a given plane, and denoted by the abbreviation CAR ("Crack Area Ratio").

The CAR criterion, well known to a person skilled in the art, makes it possible to quantify the extent of internal cracking, which can vary between 0% for an absence of cracking, to 100% for a sample that is completely cracked. These tests are denoted "cracking tests" in the remainder of the example.

For the same test conditions (same pH and same partial pressure of H$_2$S), tests according to the invention were conducted using a hollow sensor produced from the same steel, in order to determine the hydrogen equilibrium pressure (Pe) reached under the test conditions. These tests are denoted "pressure measurement tests" in the remainder of the example.

Figure 6:
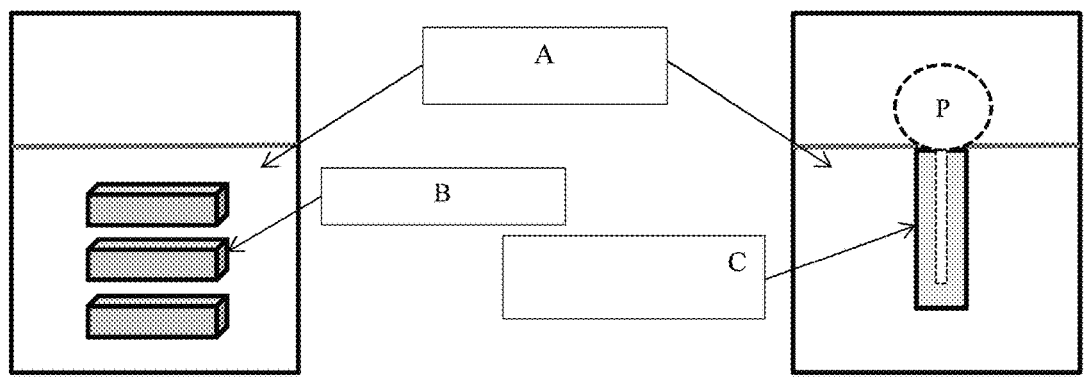
FIG. 6 shows in diagrammatic form an example of the methodology followed in order to carry out Example 2 with a first part of the experiment using coupons of the steel to be investigated (B), and a second part of the experiment using the sensor according to the invention (C), both being submerged in an aggressive medium containing hydrogen (A).

FIG. 6 illustrates the two types of tests carried out.

The crack area results for this steel, obtained from cracking tests under different test conditions, are given in Table 1 below.

As expected, the harshness of the test environment varies significantly with the pH of the solution, with a threshold at pH 6 above which no cracking is detected.

TABLE 1

Correlation between the pH of the test environment and the CAR (measured by cracking tests) as well as the H$_2$ equilibrium pressure (Pe) (measured by pressure measurement tests)

| pH | 4.5 | 5.5 | 6 | 6.5 |
|---|---|---|---|---|
| CAR (%) | 25 | 5 | 0 | 0 |
| Pe (bar) | >500 | 160 | 40 | 3 |

For this steel, and in the test medium containing 100 mbar of H$_2$S, a series of pressure measurement tests was conducted using a hollow sensor device according to the invention, in order to determine the equilibrium pressures (Pe) corresponding to the different pH levels.

In order to avoid cracking the steel bodies during pressure measurement tests, the sampling was carried out in an area of steel at a distance from the center of the plate, which is the most susceptible with respect to hydrogen embrittlement due to a higher concentration of inclusions.

Despite these precautions, certain pressure measurement tests carried out at pH 4.5 had to be interrupted due to leaks associated with cracks in the body of the sensor.

Table 1 thus correlates the crack area (CAR) with the equilibrium pressure (Pe) for this low-alloy steel with a ferrito-pearlitic microstructure exposed to aqueous media containing 35 g/L of NaCl under 100 mbar of H$_2$S and at different pH values.

Figure 3:
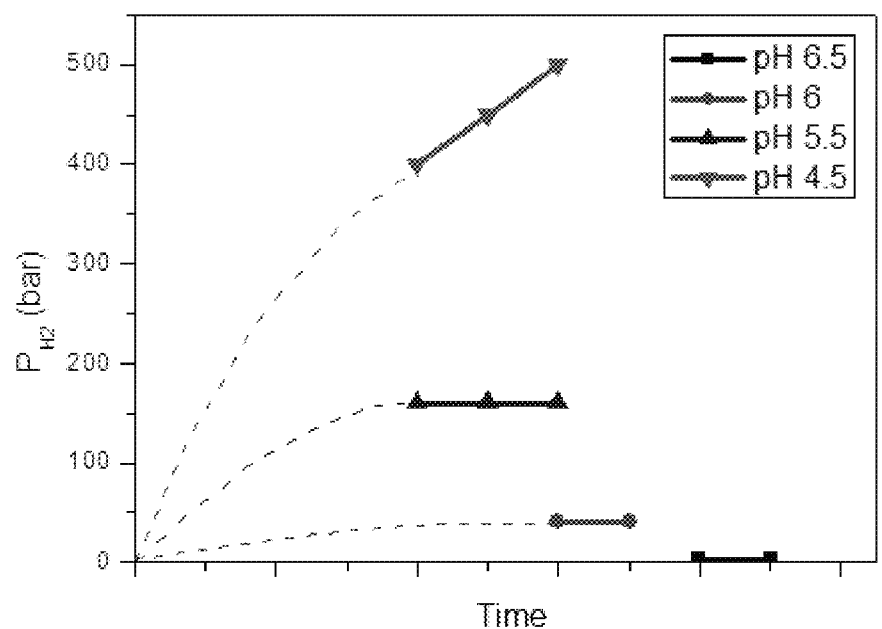
FIG. 3 shows an example of measurements of equilibrium pressure in the hollow sensor according to the invention made from low-alloy ferrito-pearlitic steel exposed to corrosive solutions at different pHs and under 100 mbar of $H_2S$. This type of environment is known to promote the entry of hydrogen into the steel. It originates in this case from the electrochemical proton reduction reaction (H++e−→H).
Figure 4:
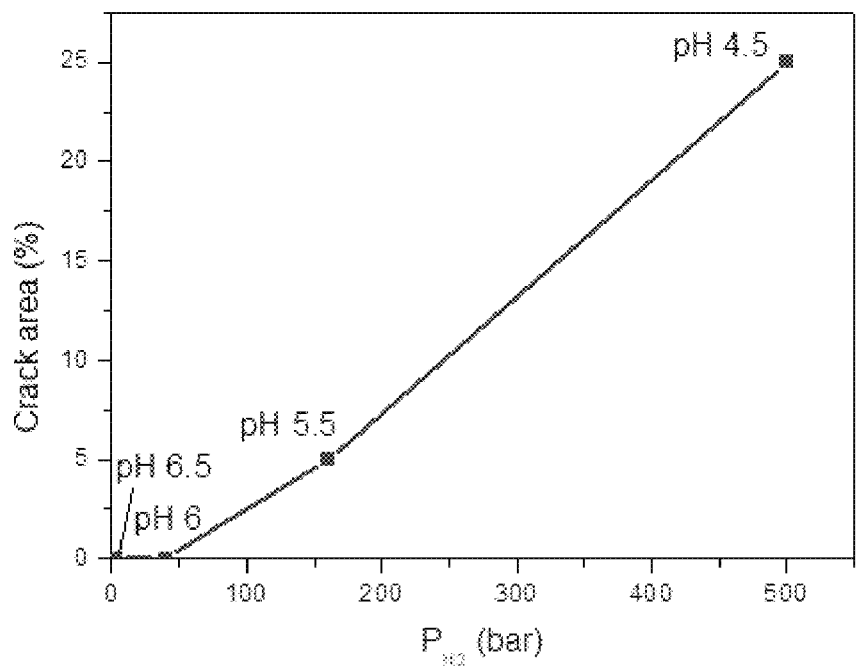
FIG. 4 shows an example of the connection between the crack area and equilibrium pressure for a low-alloy ferrito-pearlitic steel exposed to a solution of water at different pH levels and under $H_2S$ at 100 mbar.

The results are illustrated by FIGS. 3 and 4.

By comparing these equilibrium pressure measurements (pressure measurement tests) with the measurements of the crack area (cracking tests), the conclusion can be reached that for this steel, the crack-resistance limit corresponds to a hydrogen pressure threshold Ps of 40 bar, as shown in FIG. 4. FIG. 4 establishes the link existing for a given steel between the crack area and the H$_2$ pressure in the embrittlement sensor.

An embrittlement sensor constructed in this grade of steel can thus now be used in any hydrogenating environment, in order to verify that the threshold pressure (Ps) of 40 bar is not exceeded.

This principle was therefore used for a test at 10 mbar of H$_2$S and at pH 6.

Figure 5:
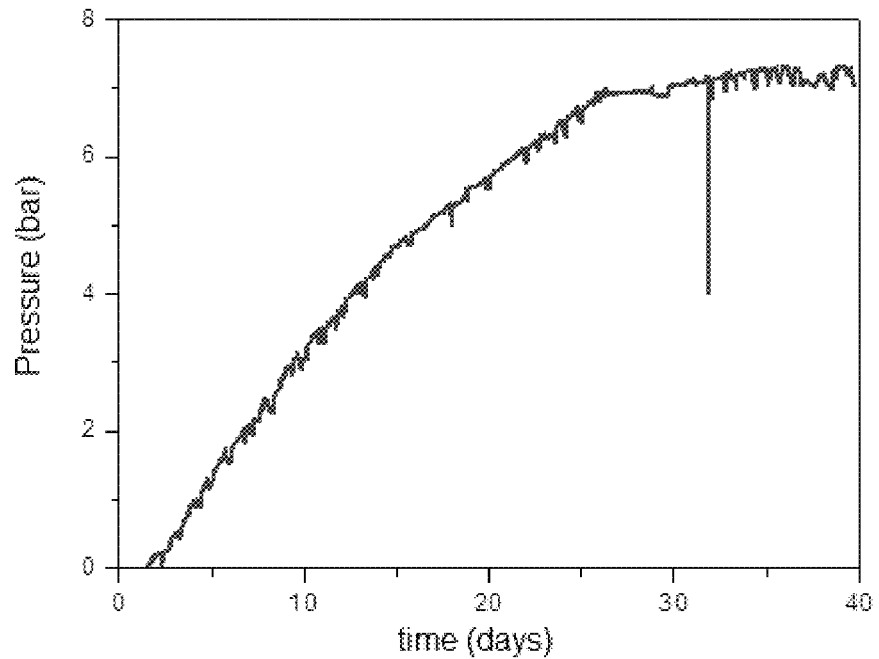
FIG. 5 shows an example of the change in the internal pressure in a hollow sensor made from low-alloy ferrito-pearlitic steel according to the invention. This sensor is subject to a corrosive environment constituted by water at 35 g/L NaCl at pH 6 and containing dissolved $H_2S$ at 10 mbar. This type of environment is known to promote the entry of hydrogen into the steel. It originates in this case from the electrochemical proton reduction reaction (H++e−→H).

The pressure change curve is shown in FIG. 5.

It is very clearly apparent that the equilibrium pressure (Pe) is established under these conditions at 7 bar, well below the threshold of 40 bar established for this material. In this case, the use of the sensor according to the invention leads to the prediction of an absence of the risk of cracking.

Cracking tests conducted under these same conditions have confirmed the absence of cracking, as predicted by the measurements carried out using the embrittlement sensor.

The invention claimed is:

1. A sensor for measuring a risk of hydrogen embrittlement of industrial equipment including a metallic wall in a reactor or in a pipeline comprising:
    a body having a closed cavity including an end containing a pressure sensor which measures pressure within the closed cavity;
    the metallic wall having a wall thickness measured between inner and outer surfaces thereof; and wherein
    a ratio of thickness of the metallic wall to thickness of the industrial equipment ranges from 1/3 to 1/10.

2. The sensor in accordance with claim 1 wherein the ratio of thickness of the metallic wall to the industrial equipment ranges from 1/4 to 1/50.

3. The sensor in accordance with claim 1 wherein the metal used to produce the sensor is the same metal used in the industrial equipment.

4. The sensor in accordance with claim 2 wherein the metal used to produce the sensor is the same metal used in the industrial equipment.

5. The sensor in accordance with claim 1 wherein the metallic wall is part of the reactor.

6. The sensor in accordance with claim 2 wherein the metallic wall is part of the reactor.

7. The sensor in accordance with claim 3 wherein the metallic wall is part of the reactor.

8. The sensor in accordance with claim 4 wherein the metallic wall is part of the reactor.

9. The sensor in accordance with claim 1 wherein the metallic wall is part of the pipeline.

10. The sensor in accordance with claim 2 wherein the metallic wall is part of the pipeline.

11. The sensor in accordance with claim 3 wherein the metallic wall is part of the pipeline.

12. The sensor in accordance with claim 4 wherein the metallic wall is part of the pipeline.

13. A method for measuring a risk of hydrogen embrittlement of industrial equipment including a metallic wall in a reactor or in a pipeline comprising:
    (1) performing cracking tests in hydrogenating environments having the risk of hydrogen embrittlement and obtaining from test conditions for which cracking is absent and for which cracking conditions are present;
    (2) in hydrogenating environments identical to step (1) performing pressure tests with a sensor in accordance with claim 1 containing a metal used in step (1) and measuring H$_2$S equilibrium pressure (Pe) for each hydrogenating environment;

(3) for each hydrogenating environment comparing results of the cracking tests of step (1) and pressure measurement tests of step (2) and determining a minimum pressure which is a threshold pressure for cracking resistance corresponding to conditions for which cracking is present;

(4) exposing the sensor which includes a metal identical to the metal used for testing in step (2) in a given environment and monitoring a change over time of pressure in the sensor until the pressure reaches a constant plateau; and (5) comparing an equilibrium value with the threshold pressure obtained in step (3) to assess if the metal has a risk of hydrogen embrittlement in the hydrogenating environment.

14. The method in accordance with claim 13 comprising:

assessing risk of hydrogen embrittlement of steel used in the reactor wall of a pipeline wall subject to environments containing $H_2$ or $H_2S$ and having a pH from 3 to 8 with the sensor according to claim 1.

15. A method in accordance with claim 13 comprising:

monitoring an environment of an industrial installation utilizing steel including an aqueous medium containing dissolved $H_2S$ to assess risk of embrittlement of the steel at the industrial installation.

16. A method for assessing risk of hydrogen embrittlement in accordance with claim 13 comprising:

monitoring an environment of an industrial installation at which industrial equipment is located which uses steel including a gaseous medium found in refining processes to assess the risk of embrittlement of steel in the industrial equipment.

* * * * *